United States Patent [19]
Blass

[11] Patent Number: 4,878,905
[45] Date of Patent: Nov. 7, 1989

[54] GASTROINTESTINAL MODULE: A NONSURGICAL IMPLANT

[76] Inventor: Karl G. Blass, University of Regina, Regina, Saskatchewan, Canada, S4S 0A2

[21] Appl. No.: 230,686

[22] Filed: Aug. 10, 1988

Related U.S. Application Data

[63] Continuation of Ser. No. 11,476, Feb. 5, 1987, abandoned.

[30] Foreign Application Priority Data

Feb. 7, 1986 [GB] United Kingdom ................. 8603099

[51] Int. Cl.⁴ ........................ A61K 9/22; A61M 31/00
[52] U.S. Cl. ................................. 604/891.1; 604/285; 604/288
[58] Field of Search ............................. 604/14, 27–28, 604/48, 49, 54, 55, 57, 60, 80, 93, 96, 103, 104, 105, 257, 258, 261, 282, 285, 286, 287, 288, 891.1, 890.1; 128/129, 130, 638

[56] References Cited

U.S. PATENT DOCUMENTS

| 1,561,020 | 11/1925 | Pond | 604/287 |
|---|---|---|---|
| 2,498,692 | 2/1950 | Mains | 604/96 |
| 2,671,451 | 3/1954 | Bolger | 604/288 |
| 2,773,502 | 12/1956 | Kaslow et al. | 128/638 |
| 3,312,215 | 4/1967 | Silber | 604/104 |
| 3,483,859 | 12/1969 | Pittman | 128/638 |
| 3,811,423 | 5/1974 | Dickinson et al. | 604/55 |
| 4,315,509 | 2/1982 | Smit | 604/54 |
| 4,531,936 | 7/1985 | Gordon | 604/49 |
| 4,687,480 | 8/1987 | Laby et al. | 604/105 |
| 4,731,054 | 3/1988 | Billeter et al. | 604/93 |

Primary Examiner—C. Fred Rosenbaum
Assistant Examiner—Sharon Rose
Attorney, Agent, or Firm—Murray E. Thrift; Stanley G. Ade; Adrian D. Battison

[57] ABSTRACT

A nonsurgically implanted gastrointestinal module is described. The module consists of an ellipsoidal or spherical collapsible gastric anchor, a tether device, and an intestinal payload module. The device is inserted into the stomach via a gastric intubation technique. The gastric anchor unfolds within the gastric cavity and lodges itself prior to the sphincter. The smaller intestinal module passes through the sphincter and unfolds within the confines of the intestine. The intestinal module is held in place via a tether which binds the gastric anchor to the intestinal payload module. The intestinal module may contain slow release medicaments, bound enzymes, cofactors, buffers, microorganisms and the like. Thus biochemical processes of the intestine may be modified, and these in turn may affect other body compartments. The gastrointestinal module may be removed with a retrieval hook via a gastric intubation technique.

12 Claims, 3 Drawing Sheets

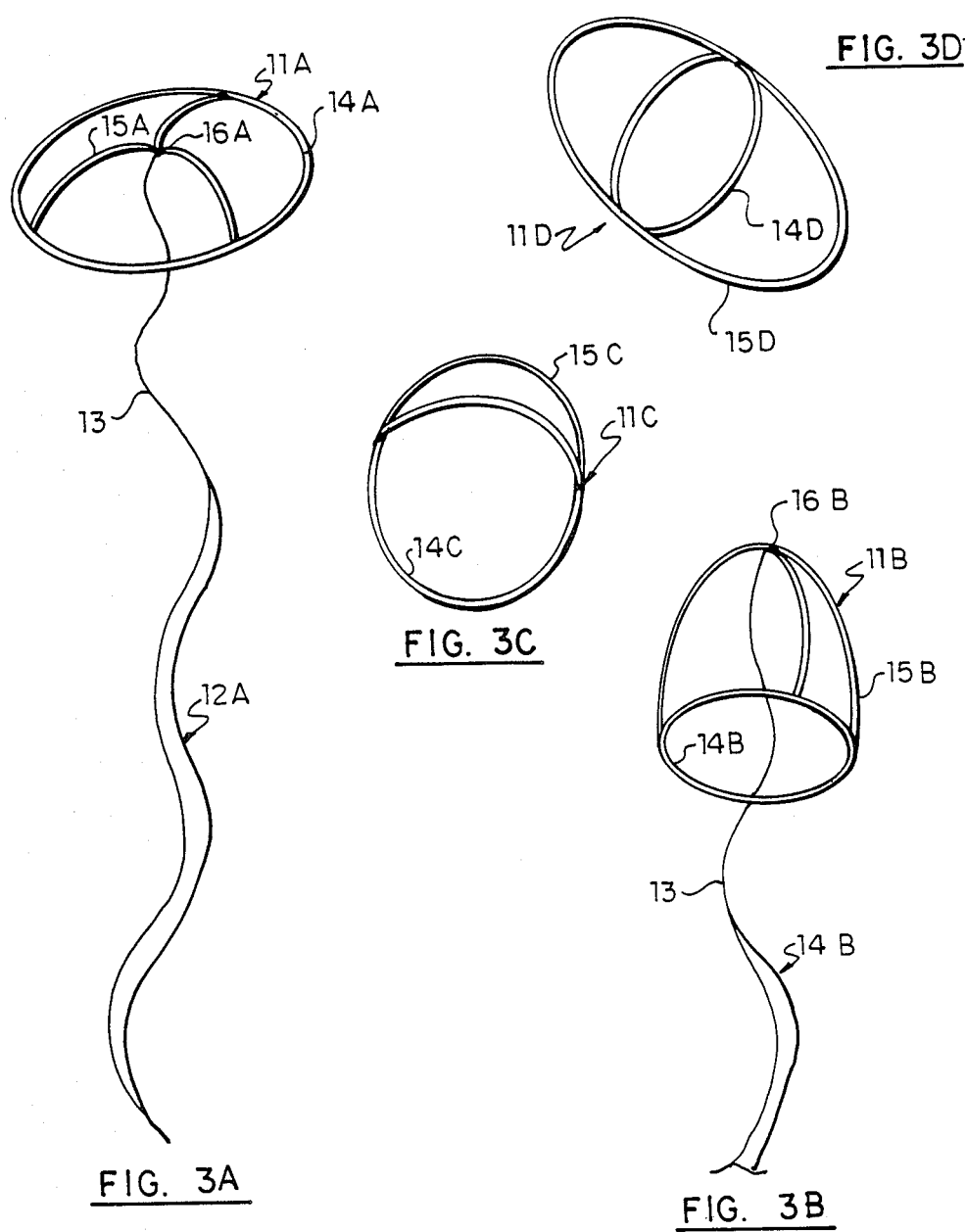

GASTROINTESTINAL MODULE: A NONSURGICAL IMPLANT

This application is a continuation of application Ser. No. 011,476, filed Feb. 5, 1987, now abandoned.

BACKGROUND OF THE INVENTION

The invention described herein relates to a new and useful collapsible ellipsoidal or spherical gastric anchoring device. The device permits non-surgical implantation of gastrointestinal modules containing slow release medicaments, bound enzymes, nonpathogenic microorganisms, including buffers, cofactors and/or absorbents as required.

SUMMARY OF THE INVENTION

The gastrointestinal module consists of an ellipsoidal or spherical gastric anchor, a tether device and an intestinal payload module. All three components may of course be constructed as one seamless unit. The gastric anchor is a collapsible device containing two, three or more ribs which come together at the top dome. The opposite ends of the ribs fasten to a loop at the bottom. The tether attaches to the underside of the dome and passes through the bottom loop. The intestinal payload module in turn is fastened to the end of the tether. The intestinal module will likely be long and narrow somewhat resembling a tapeworm.

In accordance with the invention there is provided a gastrointestinal module consisting of a collapsible ellipsoidal or spherical gastric anchor with an attached tether device and an intestinal payload module secured to said tether, said intestinal payload module being designed to alter biochemical processes within the intestine. Means are provided for maintaining the components in the collapsed condition until implanted and may take the form of encapsulating said component individually in a material such as gelatin .

The principal advantage of the invention is to be able to implant or emplace a gastrointestinal module without surgery, said module being disposable.

Another advantage of the invention is to provide a device of the character herewithin described which is simple in construction, economical in manufacture and otherwise well suited to the purpose for which it is designed.

BRIEF DESCRIPTION OF THE DRAWINGS

With the foregoing in view and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

FIG. 3A is a partially schematic view of an alternative embodiment.

FIG. 3B is a fragmentary partially schematic view of a further embodiment.

FIG. 3C is a schematic representation showing a further embodiment of the anchor component.

FIG. 3D is a schematic representation showing a still further embodiment of the anchor component.

In the drawings like characters of reference indicate corresponding parts in the different figures.

DETAILED DESCRIPTION

Figure 1A:
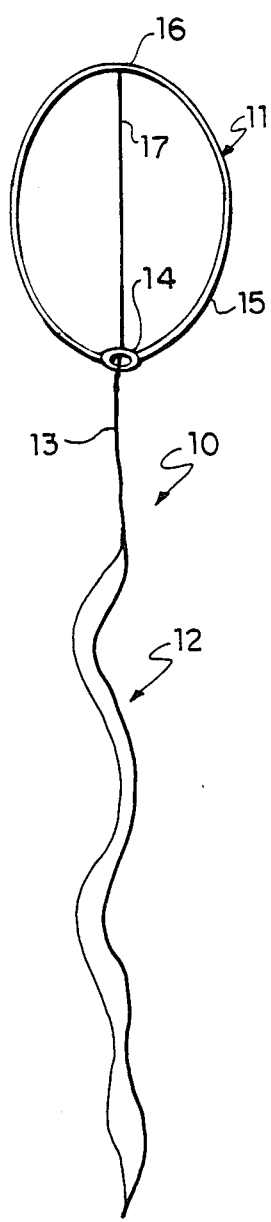
FIG. 1A is a schematic side elevation of the invention shown in the expanded position.

Proceeding therefore to describe the invention in detail, the gastrointestinal module is collectively identified by reference character 10 and includes an anchor component collectively designated 11, an intestinal payload component collectively designated 12 and a flexible tether illustrated by reference character 13.

All of the components are preferably formed from a variety of medical grade plastics possessing desirable characteristics. These materials should, of course, be inert, stable and non-toxic to body fluids and tissues, and by way of example, one such material is trade-named "Silastic" and produced by the Dow Corning Corporation, Midland, Michigan.

The preferred embodiment of the gastric anchor 11 is shown in FIG. 1A. It consists of a base ring 14 having a plurality of curved ribs 15 extending upwardly therefrom in spaced apart relationship, terminating in an apex 16 with the natural resiliency of the material forming an ellipsoidal configuration as clearly shown.

The tether 13 passes freely through the ring 14 and is secured by the upper end 17 to the aforementioned apex 16 of the ribs.

The intestinal payload component 12 is of an elongated flexible configuration similar to a tapeworm and contains the necessary materials designed to alter the biochemical processes within the intestine and to be released therefrom by various well-known means such as diffusion or the like through the wall of the component.

Prior to insertion, both components 11 and 12 are collapsed and maintained in the collapsed position until inserted within the gastric cavity and intestine respectively as will hereinafter be described.

Figure 1B:
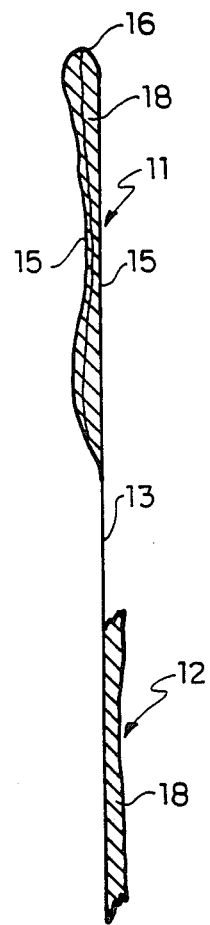
FIG. 1B is a fragmentary schematic representation of FIG. 1A with the components shown in the collapsed or encapsulated position.

Reference character 18 represents an encapsulating coating which maintains the components in the collapsed position illustrated schematically in FIG. 1B and such an encapsulating coating may consist of gelatin which is dissolvable by hydrolysis once emplaced. Of course, other encapsulating materials may be used.

The components 11 and 12 together with the tether 13 may be formed as a one-piece unit and should, of course, be without seams or any projecting edges to minimize friction and to avoid damage to the tissues and the ribs 15 would of course be widely spaced so as not to restrict the passage of the nutrients into the intestine.

Figure 1C:
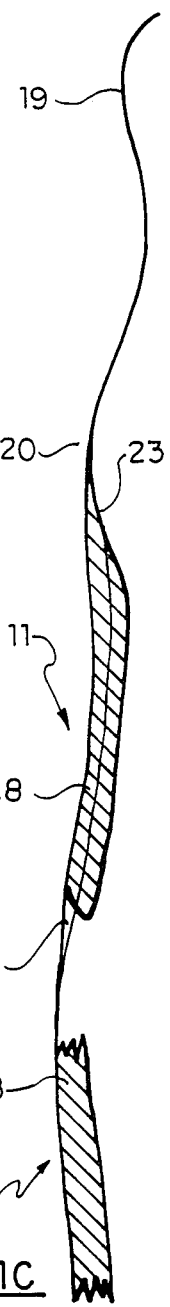
FIG. 1C is a view similar to FIG. 1B, but showing one method of implanting the module.
Figure 2B:
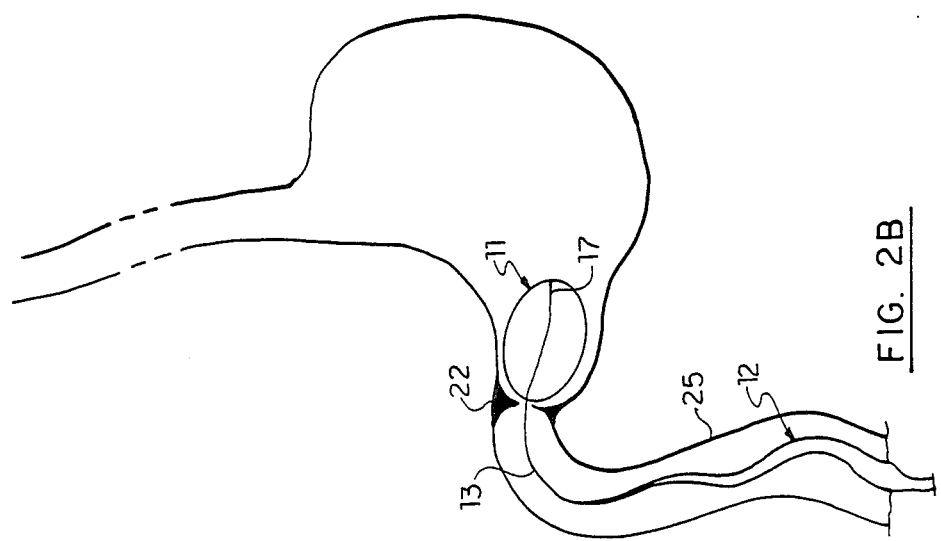
FIG. 2B is a view similar to FIG. 2A, but showing the components in the expanded emplaced position.
Figure 2A:
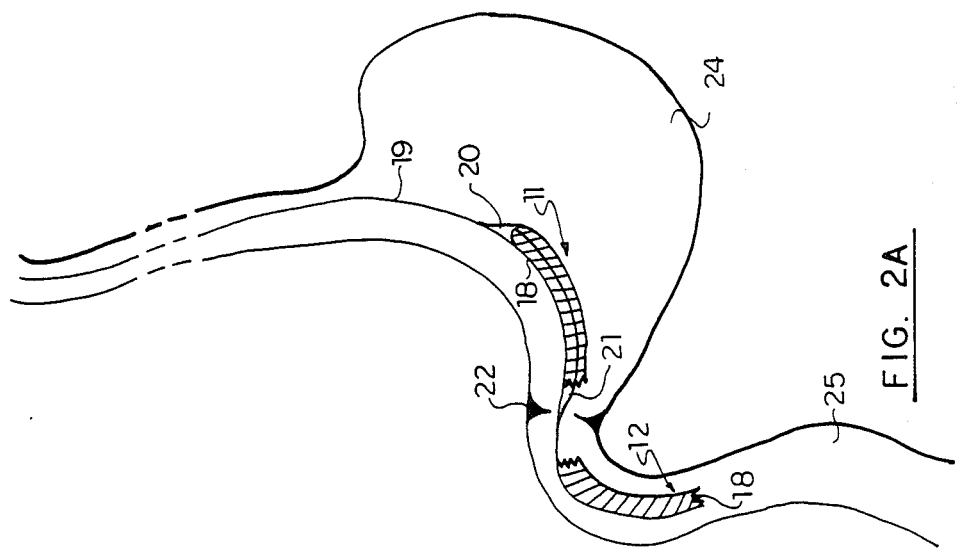
FIG. 2A is a schematic representation showing the device implanted with the components encapsulated or collapsed.

The device may be implanted via a gastric intubation technique as illustrated schematically, for example, in FIGS. 1C and 2A.

By way of example only, the intubation tube 19 of conventional construction may be forked at the insertion end and as illustrated by reference character 20. The long arm 21 of the forked end engaging the collapsed component 12 is passed through the sphincter shown schematically by reference character 22 while the shorter arm 23 engaging the anchor component 11 remains in the gastric cavity indicated by reference character 24. Reference character 25 indicates the intestine into which the payload component 12 is engaged.

Once the encapsulating material is dissolved, the payload module 12 would unfold in the intestine 25 while the gastric anchor component 11 would unfold within the stomach or gastric cavity 24 and take up the position shown in FIG. 2B.

This would release both the spherical anchor and the intestinal module from the gastric intubation tube 19 which would then be removed while the anchor component 11 would lodge itself prior to the sphincter 22 as shown in FIG. 2B, thus holding the intestinal payload module 12 by means of the tether device 13.

The intestinal module would exert a downward force upon the apex 16 of the gastric anchor component 11 via the tether 13 which force would assist in maintaining the spherical shape of the gastric anchor.

Furthermore, the ribs 15 of the gastric anchor component 11 would also act as shock absorbers for forces exerted by the intestinal component 12 and these anchor ribs 15 are so shaped as to distribute the anchoring forces over the gastric wall. Thus, the ribs should preferably be somewhat flattened and be without edges and seams to minimize friction and the like as hereinbefore discussed.

As mentioned previously, the intestinal component 12 may contain slow release medicaments, bound enzymes, cofactors, buffers, microorganisms and the like so that the biochemical processes of the intestine may be modified and in turn, may affect other body compartments.

When the treatment is completed, the gastrointestinal module may be removed with a conventional retrieval hook via a gastric intubation technique.

FIGS. 3B, 3C and 3D show the configuration of other anchor components 11B, 11C and 11D respectively.

In FIG. 3B, the base ring is indicated by reference character 14B and the upwardly curving ribs by reference character 15B, terminating in the apex 16B to which the tether 13 is secured and depends downwardly freely through the ring 14B.

FIG. 3C shows a somewhat similar configuration with the base ring 14C and the curved ribs 15C which are more circular in configuration than the domed configuration shown in FIG. 3B.

In FIG. 3D, the ring is illustrated by reference character 14D with the domed ribs 15D being ellipsoidal and extending upon both sides of the ring.

FIG. 3A shows the ring at 14A with the flexible ribs 15A extending equally spaced around the ring terminating in the apex 16A and with the tether 13 being secured to the intestinal component 12, all of which is shown in the unfolded position.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A gastrointestinal module comprising in combination a collapsible gastric anchor component including a flexible cavity-wall gastric engaging member and a plurality of flexible, resilient ribs extending upwardly therefrom converging to a common apex, an intestinal payload component containing releasable medicaments for altering the biochemical process within the bowel, tether means secured to the anchor component only adjacent said apex and extending downwardly therefrom through and unconnected to said gastric-cavity wall engaging member to the payload component connected to and supporting said payload component from said anchor component, and means maintaining said anchor component in a collapsed condition until implanted.

2. The invention according to claim 1 in which said payload comprises an elongated flexible envelope secured by the upper end thereof to said tether means.

3. The invention according to claim 1 in which said tether means includes a relatively thin flexible connecting cable.

4. The invention according to claim 2 in which said tether means includes a relatively thin flexible connecting cable.

5. The invention according to claim 1 in which said means maintaining said components in the collapsed condition until implanted comprises encapsulating said components individually in an envelope of material dissolvable when in position, by hydrolysis of said material.

6. The invention according to claim 2 in which said means maintaining said components in the collapsed condition until implanted comprises encapsulating said components individually in an envelope of material dissolvable when in position, by hydrolysis of said material.

7. The invention according to claim 5 in which said material is gelatin.

8. The invention according to claim 6 in which said material is gelatin.

9. The invention according to claim 1 in which said gastro-cavity-wall engaging member comprises a base ring and the ribs comprise a plurality of spaced apart ribs curving upwardly from said ring to said apex.

10. The invention according to claim 2 in which said gastro-cavity-wall engaging member comprises a base ring and the ribs comprise a plurality of spaced apart ribs curving upwardly from said ring to said apex.

11. The invention according to claim 5 in which said gastro-cavity-wall engaging member comprises a base ring and the ribs comprise a plurality of spaced apart ribs curving upwardly from said ring to said apex.

12. The invention according to claim 6 in which said gastro-cavity-wall engaging member comprises a base ring and the ribs comprise a plurality of spaced apart ribs curving upwardly from said ring to said apex.

* * * * *